US010583461B2

(12) United States Patent
Miriyala et al.

(10) Patent No.: US 10,583,461 B2
(45) Date of Patent: Mar. 10, 2020

(54) CONFIGURABLE PULSER CIRCUIT OPERABLE ACROSS A RANGE OF SUPPLY VOLTAGES

(71) Applicant: TEXAS INSTRUMENTS INCORPORATED, Dallas, TX (US)

(72) Inventors: Aravind Miriyala, Bengaluru (IN); Naveen Kumar Ginige, Bengaluru (IN); Vajeed Nimran, Bengaluru (IN); Saugata Datta, Kolkata (IN); Shabbir Amjhera Wala, Bengaluru (IN)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 256 days.

(21) Appl. No.: 15/852,018

(22) Filed: Dec. 22, 2017

(65) Prior Publication Data

US 2019/0009301 A1    Jan. 10, 2019

(30) Foreign Application Priority Data

Jul. 6, 2017    (IN) .............................. 201741023734

(51) Int. Cl.
*B06B 1/02*    (2006.01)
*H03K 17/687*    (2006.01)
*A61B 8/00*    (2006.01)

(52) U.S. Cl.
CPC ....... *B06B 1/0215* (2013.01); *H03K 17/6871* (2013.01); *A61B 8/4483* (2013.01);
(Continued)

(58) Field of Classification Search
CPC .............. B06B 1/0215; H03K 17/6871; H02H 7/1203; H02H 11/002
(Continued)

(56) References Cited

U.S. PATENT DOCUMENTS 7,824,335 B2 * 11/2010 Wodnicki ................. A61B 8/00
                                                  600/437
9,473,136 B1 * 10/2016 Chen ........................ A61N 7/02
(Continued)

FOREIGN PATENT DOCUMENTS

JP    H02151264    6/1990
JP    2004328413    11/2004

OTHER PUBLICATIONS

International Search Report for corresponding PCT Application No. PCT/US2018/040990, dated Sep. 27, 2018 (2 pages).

*Primary Examiner* — Alfonso Perez Borroto
(74) *Attorney, Agent, or Firm* — John R. Pessetto; Charles A. Brill; Frank D. Cimino

(57) ABSTRACT

A semiconductor device includes a trim storage and an encoder. The trim storage stores trim values. The encoder determines a magnitude of a supply voltage, determines a magnitude of a handle voltage, determines a source-to-handle voltage of a first transistor, and determines a source-to-handle voltage of a second transistor. Further, the encoder determines a target number of selectable first transistor units comprising the first transistor to select for the first transistor. Based on a trim value from the trim storage, the source-to-handle voltage of the first transistor and the source-to-handle voltage of the second transistor, the encoder determines a target number of selectable second transistor units comprising the second transistor to select for the second transistor. The encoder asserts control signals to select the target number of selectable first transistor units and the target number of selectable second transistor units.

20 Claims, 4 Drawing Sheets

(52) U.S. Cl.
CPC .. *B06B 2201/76* (2013.01); *H03K 2217/0063* (2013.01); *H03K 2217/0072* (2013.01)

(58) Field of Classification Search
USPC .......................................................... 307/115
See application file for complete search history.

(56) References Cited

U.S. PATENT DOCUMENTS

| | | | | |
|---|---|---|---|---|
| 10,175,347 B2* | 1/2019 | Chen | ..................... | G01S 7/5273 |
| 2004/0254459 A1* | 12/2004 | Kristoffersen | ........ | B06B 1/0215 |
| | | | | 600/437 |
| 2007/0103186 A1 | 5/2007 | Clements et al. | | |
| 2009/0250729 A1* | 10/2009 | Lemmerhirt | ............. | A61B 8/00 |
| | | | | 257/254 |
| 2010/0317972 A1* | 12/2010 | Baumgartner | ....... | G10K 11/002 |
| | | | | 600/459 |

* cited by examiner

CONFIGURABLE PULSER CIRCUIT OPERABLE ACROSS A RANGE OF SUPPLY VOLTAGES

CROSS REFERENCE TO RELATED APPLICATIONS

This application claims priority to India Provisional Application No. 201741023734, filed Jul. 6, 2017, which is incorporated herein by reference

BACKGROUND

Ultrasound machines are widely used as medical diagnostic equipment. An ultrasound system front-end includes a transmitter, which drives a transducer, and a receiver which receives the reflected acoustic signal. The transmitter may comprise an amplifier such as a pulser amplifier or a linear amplifier. A pulse amplifier includes high voltage metal oxide semiconductor field effect transistors (HV MOSFETs) which are toggled on and off by way of control signals. An important performance specification for a pulse amplifier in an ultrasound machine is that, at least in some applications, HD2 (i.e., second harmonic distortion) should be no greater than −40 dBc at 5 MHz. Failure to comply with that performance specification may detrimentally impact the accuracy of the machine.

SUMMARY

In one example, a semiconductor device includes a high side transistor comprising a plurality of selectable first transistor units and a low side transistor coupled in series with the high side transistor. The low side transistor comprises a plurality of selectable second transistor units. The semiconductor device includes trim storage configured to store trim values and an encoder. The encoder is configured to determine a magnitude of a supply voltage, determine a magnitude of a handle voltage, determine a source-to-handle voltage of the high side transistor, determine a source-to-handle voltage of the low side transistor, determine a target number of the selectable first transistor units to select for the high side transistor, determine a target number of the selectable second transistor units to select for the low side transistor, and assert control signals to gate drivers associated with the selectable first and second transistor units to select the target number of selectable first transistor units and the target number of selectable second transistor units.

In yet another example, a method comprises setting a first source-to-handle voltage for a first transistor. The first transistor comprises a plurality of selectable first transistor units. The method also includes setting a second source-to-handle voltage for a second transistor coupled to the first transistor. The second transistor comprises a plurality of selectable second transistor units. The method includes measuring a first saturation current of the first transistor, measuring a second saturation current of the second transistor, determining a number of the plurality of selectable first transistor units, determining a number of the plurality of selectable second transistor units, setting a third source-to-handle voltage for the first transistor, setting a fourth source-to-handle voltage for a second transistor, measuring a third saturation current of the first transistor, and measuring a fourth saturation current of the second transistor. The method also includes determining trim values based on the measured first, second, third, and fourth saturation currents and storing the trim values in a memory device.

In yet another example, a semiconductor device includes a trim storage and an encoder. The trim storage stores trim values. The encoder determines a magnitude of a supply voltage, determines a magnitude of a handle voltage, determines a source-to-handle voltage of a first transistor, and determines a source-to-handle voltage of a second transistor. Further, the encoder determines a target number of selectable first transistor units comprising the first transistor to select for the first transistor. Based on a trim value from the trim storage, the source-to-handle voltage of the first transistor and the source-to-handle voltage of the second transistor, the encoder determines a target number of selectable second transistor units comprising the second transistor to select for the second transistor. The encoder asserts control signals to select the target number of selectable first transistor units and the target number of selectable second transistor units.

BRIEF DESCRIPTION OF THE DRAWINGS

For a detailed description of various examples, reference will now be made to the accompanying drawings in which.

DETAILED DESCRIPTION

The disclosed pulser transmitter for a system such as an ultrasound machine includes a high side transistor coupled in series to a low side transistor at a node. The voltage on the node toggles between two supply voltage levels. To ensure compliance with the applicable second harmonic distortion criteria (e.g., −40 dBc at 5 MHz), the rising and falling edges of the voltage waveform on the node between the transistors should match within a certain threshold value. For example, the rising edge time value should be within 1 ns of the falling edge time value.

Rise and fall times are mainly determined by the saturation current level and the on-resistance of power MOSFETs in the transmitter. However, the saturation current and the on-resistance vary with the source-to-handle voltage difference, and that voltage difference may vary from application to application. In some applications, the handle is connected to the most negative potential available in the system for the best break-down voltage. The most negative potential may be the same as the negative supply for the transmitter, or may be different than the negative pulser supply. Further, the supply voltage to the transmitter can vary from application to application. Thus, it is difficult to guarantee matching rise and fall times across supply and handle potentials.

In the disclosed embodiments, it is recognized that the saturation current of the power MOSFETs and their on-resistance influences the rise and fall times as noted above. Further, the saturation current and on-resistance vary with the magnitude of the source-to-handle voltage. Thus, the source and handle potentials are sensed and used to trim the transmitter for compliance with the applicable HD2 specification. In the disclosed embodiments, each of the power MOSFET is implemented as a plurality of selectable transistor units. The number of transistor units for each MOSFETs is selected so as to trim the mismatch in the on-resistance (termed Ron herein) and the saturation current (termed Idsat herein) at a particular supply voltage (e.g., 100V).

Figure 1:
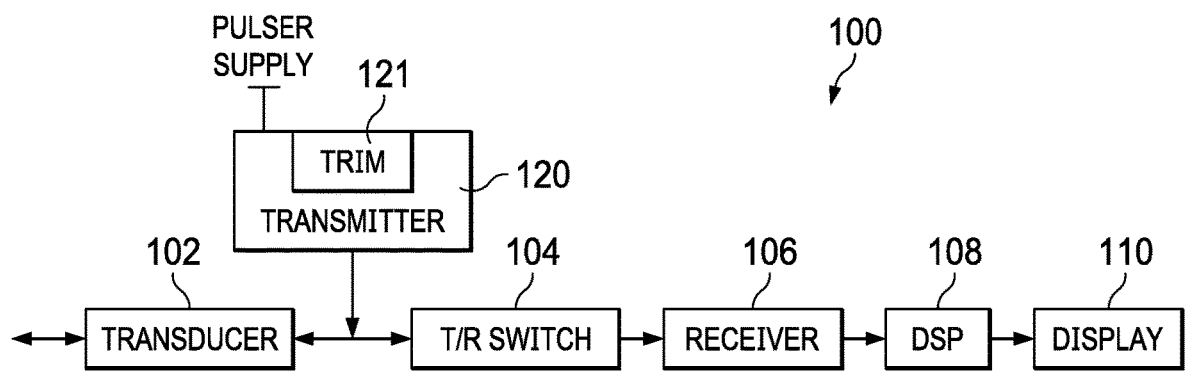
FIG. 1 illustrates an electronic system usable in an ultrasound machine in accordance with a disclosed embodiment.

FIG. 1 shows an embodiment of an electronic system 100 suitable for an ultrasound machine. The system 100 includes a transducer 102, a transmit/receive switch 104, a receiver 106, a transmitter 120, a digital signal processor (DSP) 108, and a display 110. The transmitter 120 produces high voltage signals to be supplied to the transducer 102. The transmit/receive switch 104 is open during the transmit phase so as not to cause damage to the receiver 106 from the elevated voltages produced by the transmitter 120. During a receive phase, the transmitter is turned off, and the transmit/receive switch 104 is closed to permit reflected acoustic signals detected by the transducer 102 to be provided to the receiver 106. The DSP 108 further processes the signals and generates images to be shown on display 110.

The transmitter 120 includes trim storage 121 in which values measured and/or calculated are stored. Trim storage 121 may comprise a one-time programmable memory device. The trim values may be determined at the factory prior to shipment of the system 100 (or transmitter 120) to an integrator to install the system 100 (transmitter 120) in an ultrasound machine. Examples of the trim values are described below. Upon activation of the ultrasound machine with transmitter 120 installed therein, the transmitter senses the particular pulser supply voltage provided to it and calculates the number of transmitter units to activate for each of the power MOSFETs in the transmitter 120.

Figure 2:
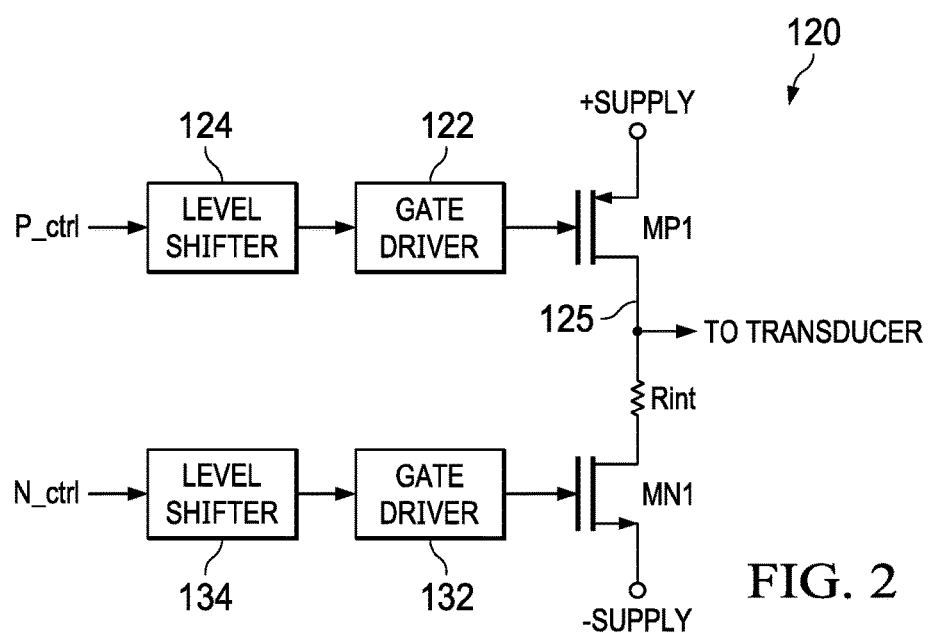
FIG. 2 shows a portion of a transmitter in the electronic system of FIG. 1 in accordance with a disclosed embodiment.

FIG. 2 shows an example of a portion of the transmitter 120. The transmitter includes a p-type MOSFET (MP1) coupled in series to an n-type MOSFET (MN1). The drains of MP1 and MN1 are connected together as shown at a node 125. Node 125 is the output of the transmitter and is coupled to the transducer 102. The source of MP1 receives the positive supply voltage and the source of MN1 receives the negative supply voltage. The positive and negative supply voltages for the transmitter may vary from application to application. In one example, the supply voltages are +100V and −100V, but can be different than that in other embodiments. In some examples, the positive supply voltage is a voltage anywhere between 3V and 100V, and the negative supply voltage is a voltage anywhere between −3V and −100V. Reference herein to "handle" refers to the back-side substrate present below buried oxide in the semiconductor device fabricated using silicon-on-insulator (SOI) process. Reference to the source-to-handle voltage refers to the voltage differences between a transistor's source and the semiconductor device's handle potential.

The gate of MP1 is driven by a gate driver 122, and the gate of MN1 is driven by a gate driver 132. A P_ctrl signal is used to turn MP1 on and off. P_ctrl is level-shifted as necessary by level shifter 124 and the output of the level shifter 124 is provided to the gate driver 122 for turning MP1 on and off. Similarly, an N_ctrl signal is used to turn MN1 on and off. N_ctrl is level-shifted as necessary by level shifter 134 and the output of the level shifter 134 is provided to the gate driver 132 for turning MN1 on and off.

Figure 3:
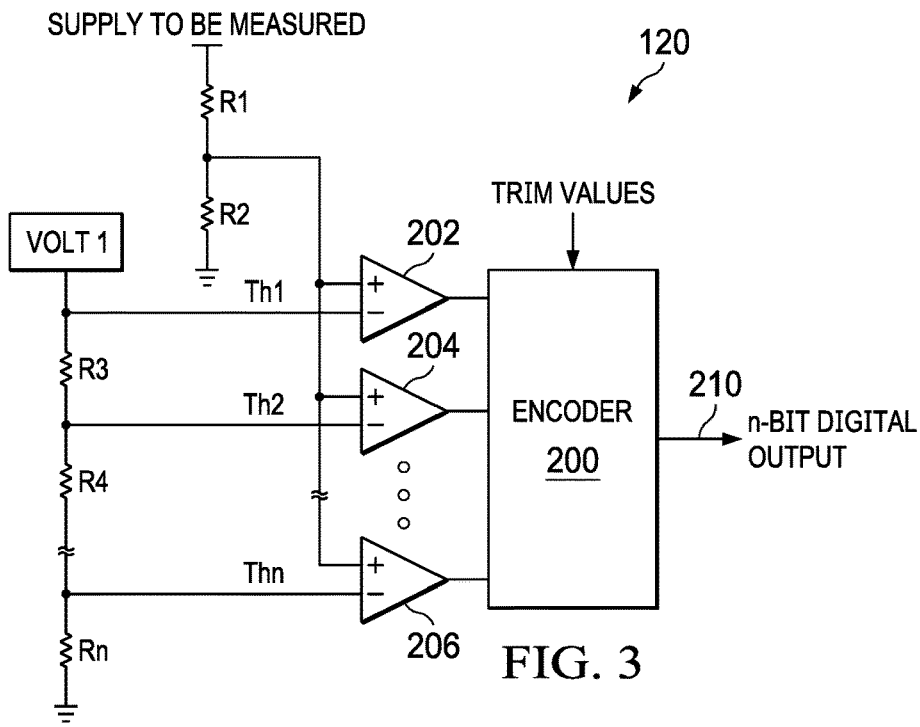
FIG. 3 also shows a portion of a transmitter in the electronic system of FIG. 1 in accordance with a disclosed embodiment.

FIG. 3 shows another portion of the transmitter 120. In this example, the transmitter includes an encoder 200 and multiple comparators 202, 204, and 206. As noted above, the transmitter 120 senses the particular supply voltage to which it is connected and configures the number of units of the power MOSFETs based on that measurement as well as the trim values. FIG. 3 shows an example of a circuit for sensing the supply voltage. The circuit shown in FIG. 3 coupled to the encoder 200 may be replicated for sensing the handle potential as well. A resistor divider comprising resistors R1 and R2 is used in this example to provide a scaled-down version of the supply voltage to the non-inverting (+) input of each of the comparators 202-206. The inverting (−) input of each comparator receives a different threshold for comparison to the scaled down supply voltage. Another resistor divider network comprising resistors R3, R4, . . . , Rn is provided to generate the various threshold voltages (Th1, Th2, . . . , Thn) from a reference voltage VOLT1. The output of each comparator in this example is a logic high if the scaled down supply voltage is greater than its corresponding threshold voltage. The output of each comparator is a logic low, however, if the scaled down supply voltage is smaller than its corresponding threshold voltage. The encoder 200 receives the bits from the comparators 202-206 as well as some or all of the trim values from trim storage 121, and generates a corresponding n-bit digital output value at 210 that specifies the number of individual transistor units to activate for each of the MP1 and MN1 MOSFET transistors as explained below. In one example, the encoder 200 may be implemented as a finite state machine.

Figure 4:
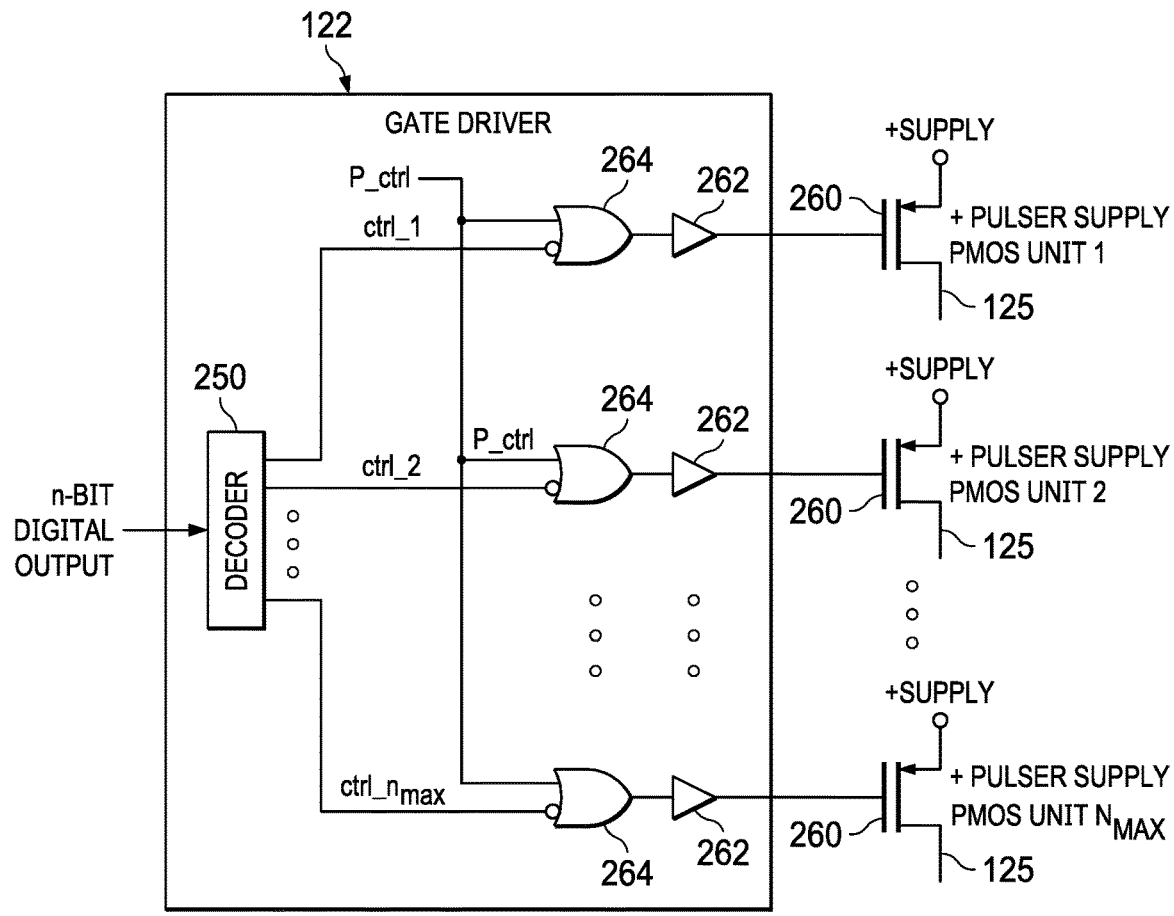
FIG. 4 also shows a portion of a transmitter in the electronic system of FIG. 1 in accordance with a disclosed embodiment.

FIG. 4 shows a portion of the transmitter 120 including the gate driver 122 coupled to the MP1 transistor. The MP1 transistor is shown in this example as a plurality of transistor units 260. The transistor units 260 are coupled in parallel with one another and through activation of the gates of the transistor units, any number of transistor units provided in the transistor for MP1 can be activated. The gate driver 122 includes a separate buffer 262 for each transistor unit 260. A logic gate 264 also is included for each buffer 262 to enable the corresponding buffer based on the P_ctrl control signal and the n-bit digital output value from the encoder 200. The decoder 250 decodes the n-bit digital output value to generate individual control signals (ctrl_1, ctrl_2, . . . , ctrl_n) for each logic gate as shown. In this example, each logic gate comprises an OR-gate with one inverted input to receive the ctrl_1, ctrl_2, . . . , ctrl_n control signals. The gate driver 132 for MN1 has the same or similar architecture as gate driver 122.

The widths of MP1 and MN1 may be chosen when designing the transmitter such that their saturation currents will match. The designer of the transmitter can use the equation for calculating the saturation current as a function of width and length of the transistor, expected threshold voltage, expected gate-to-source voltage, and other parameters to calculate the widths of MP1 and MN1. The saturation current equation may be expressed as:

$$Idsat = \frac{\mu * Cox}{2} * \frac{W}{L} * (Vgs - Vt)^2$$

where Idsat is the saturation current, μ is the mobility, Cox is the gate oxide capacitance per unit area, W is the width, L is the length, Vgs is the gate-to-source voltage, and Vt is the threshold voltage. The equation above can be solved for W given estimates of the other parameters.

Once the widths for MP1 and MN1 are chosen for saturation current matching, a resistor, Rint (FIG. 2), is added in series with MN1 so that the on-resistance of MP1 matches the on-resistance of MN1. This resistor Rint can be implemented using the N-drift resistor, which has characteristics similar to the n-drift region present in high voltage n-type MOSFETs. The gate drivers 122 and 132 also are designed for the transmitter so as to match the time delay between receipt of a control signal to turn on the corresponding transistor and the time that the gate driver asserts a gate signal to the corresponding transistor.

To an extent, saturation current and Ron of an HV MOSFET device track across process corners. This means that if, based on particular process, the saturation current for a given transistor is higher than average, Ron will tend to be lower than average. As the n-drift resistor has similar characteristics as the n-drift region of an n-type HV MOSFET, the saturation current for an n-type HV MOSFET and the resistance of the N-drift resistor also track, to an extent, across process corners. The disclosed embodiments use this relationship to facilitate the trim process for the transmitter 120.

Figure 5:
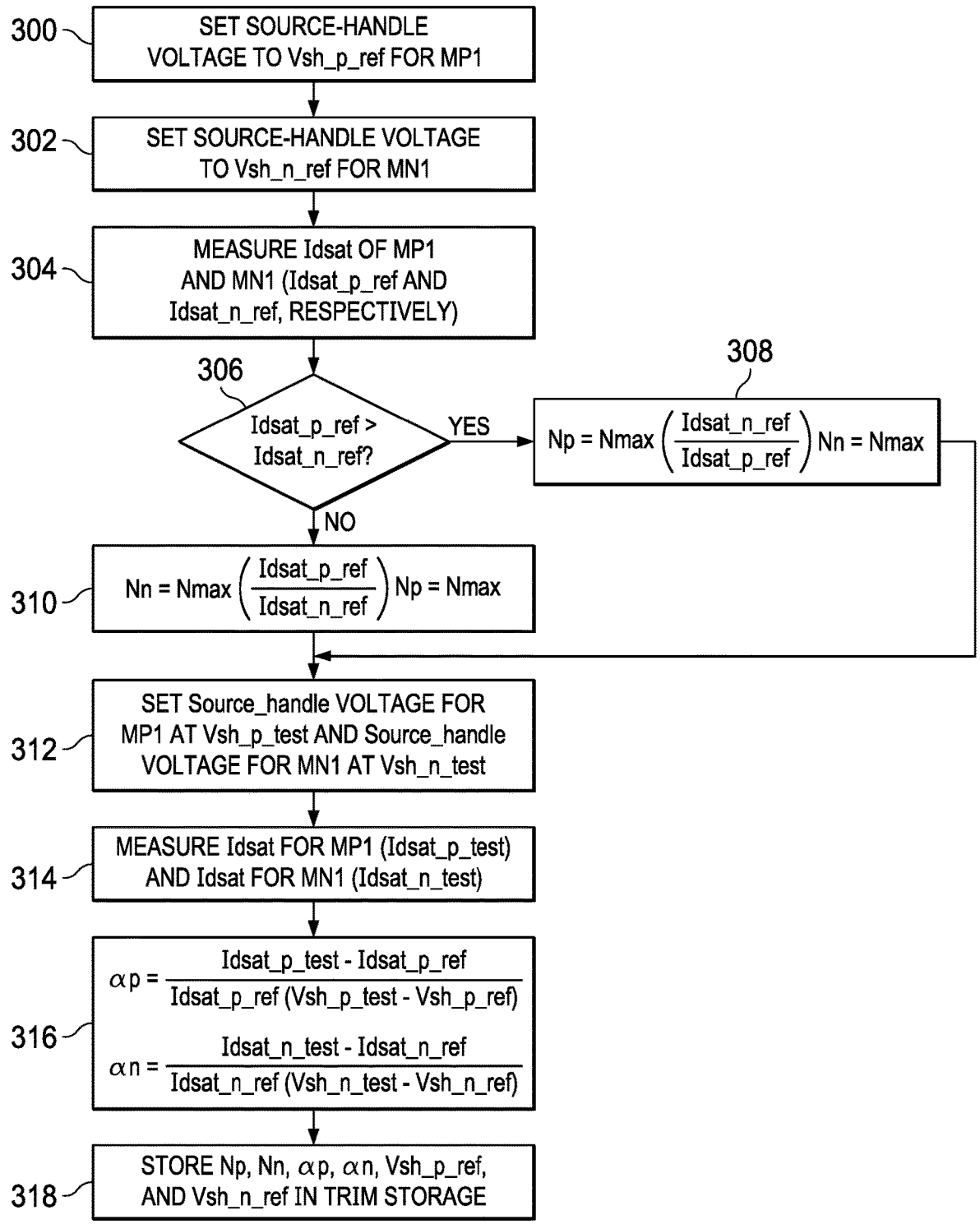
FIG. 5 shows a method for trimming the transmitter in accordance with an example.

FIG. 5 shows an example of a method of trimming the transmitter 120. The method may be performed after the transmitter is fabricated before its initial use in an ultrasound machine. In some cases, trimming may be performed at the factory where the transmitter is fabricated prior to its shipment. In other cases, trimming may be performed after shipment to the entity that installs the transmitter in the ultrasound machine but before the transmitter is actually installed in the machine. The operations may be performed in the order shown, or in a different order. Further, two or more of the operations may be performed concurrently instead of sequentially. Even if two operations are performed in order, the latter operation may begin before the former operation completes. Some of the operations of FIG. 5 may be performed by an electronic compute system (comprising a processor coupled to memory containing executable code) external to the transmitter 120.

At 300, the trim method includes setting the source-to-handle voltage to a reference voltage, Vsh_p_ref for the pMOS device MP1. In one example, the pulser supply voltage for this operation is +/−100V and the handle supply voltage is −100V which results in Vsh_p_ref being 200V. At 302, the method includes setting the source-to-handle voltage for MN1 to a reference voltage, Vsh_n_ref. In the example in which the pulser supply voltage is +/−100V and the handle supply voltage is −100V, Vsh_n_ref is 0V.

At 304, the method includes measuring Idsat for each of the MP1 and MN1 transistors (with all transistor units activated). In one example, P_ctrl and N_ctrl are provided generated such that a square wave is obtained at node 125 for a relatively short duration. By coupling a capacitor having a known capacitance to node 125 and by measuring the rise time and the fall time of the square wave at node 125, Idsat can be estimated. The measurement of Idsat for MP1 at the reference voltage (Vsh_p_ref) is referred to as Idsat_p_ref and the measurement of Idsat for MN1 at the reference voltage (Vsh_p_ref) is referred to as Idsat_n_ref.

At 306, the method determines whether, at the reference voltage, the saturation current for MP1 is greater or smaller than the saturation current for MN1. If Idsat_p_ref is greater than Idsat_n_ref, then at 308, the number of units for MN1 at the reference voltage is set at the maximum number of MN1 transistors that are available in the transmitter, that is, Nn=Nmax. The number of units for MP1 (Np) at the reference voltage is computed as Nmax times the ratio of Idsat_n_ref to Idsat_p_ref), rounded up or down as desired to an integer value.

If, however, Idsat_p_ref is smaller than Idsat_n_ref, then at 310, the number of units for MP1 (Np) at the reference voltage is set Nmax. The number of units for MN1 (Nn) at the reference voltage is computed as Nmax times the ratio of Idsat_p_ref to Idsat_p_ref), rounded up or down as desired to an integer value. Thus, at the reference condition (i.e., use of Vsh_p_ref and Vsh_n_ref), causing the number of units for MP1 to equal Np and the number of units of MN1 to equal Nn results in matching Idsat for MP1 and MN1. As Idsat and Ron track, to an extent, across process corners, Ron of MP1 and MN1 also match.

At 312, the method includes setting the source-to-handle voltage for MP1 at a test voltage designated as Vsh_p_test and setting the source-to-handle voltage for MN1 at a test voltage designated as Vsh_n_test. In one example, the pulser supply voltage for this operation is set to +/−25V and the handle supply voltage is set to −100V. At this voltage levels, Vsh_p_test is 125V and Vsh_n_test 75V.

At 314, the method includes measuring Idsat at the test voltage for each of the MP1 and MN1 transistors (with all transistor units activated). The measurement of Idsat for MP1 at the test voltage (Vsh_p_test) is referred to as Idsat_p_test and the measurement of Idsat for MN1 at the test voltage (Vsh_n_test) is referred to as Idsat_n_test. The measurements of the saturation current for MP1 and MN1 may be performed as explained above.

At 316, trim values αp and αn are computed based on the measured saturation currents at the test and reference supply voltages and the source-to-handle voltages for the test and reference conditions. In this example, the calculations for αp and αn are:

$$\alpha p = \frac{\text{Idsat\_p\_test} - \text{Idsat\_p\_ref}}{\text{Idsat\_p\_ref}(\text{Vsh\_p\_test} - \text{Vsh\_p\_ref})}$$

$$\alpha n = \frac{\text{Idsat\_n\_test} - \text{Idsat\_n\_ref}}{\text{Idsat\_n\_ref}(\text{Vsh\_n\_test} - \text{Vsh\_n\_ref})}$$

At 318, the trim values are stored in trim storage 121 within the transmitter 120. The trim values include any or all of Np, Nn, αp, αn, Vsh_p_ref, and Vsh_n_ref.

Figure 6:
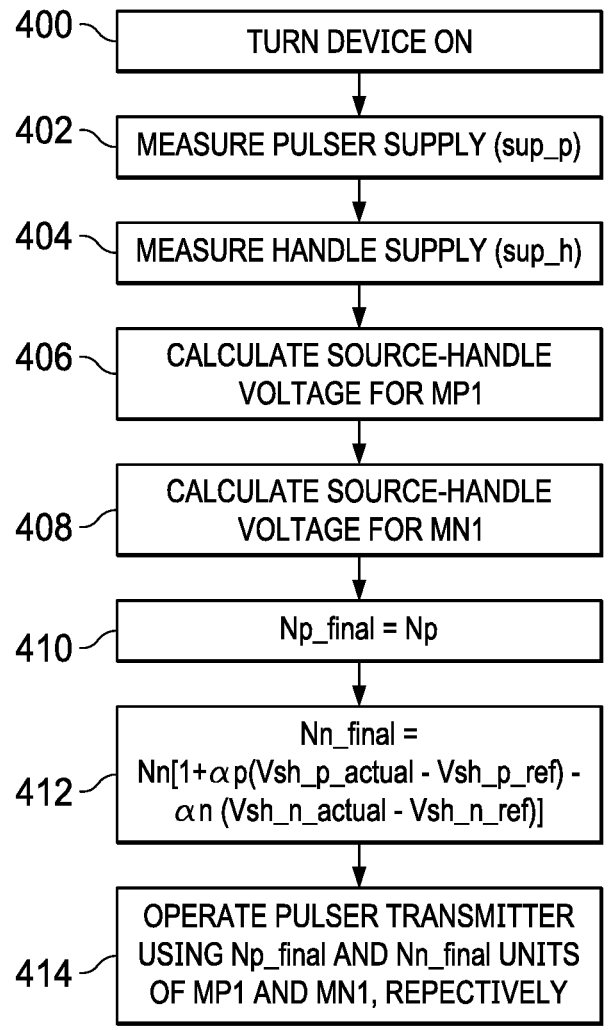
FIG. 6 shows a method for configuring the transmitter prior to its operation based on trim values determined during the method of FIG. 5 in accordance with a disclosed embodiment.

FIG. 6 shows an example of a method of configuring the transmitter 120 after it has been trimmed for use in operating a system such as an ultrasound machine. The operations may be performed in the order shown, or in a different order. Further, two or more of the operations may be performed concurrently instead of sequentially. Even if two operations are performed in order, the latter operation may begin before the former operation completes. The method of FIG. 6 measures the actual supply and handle voltages that are used for the transmitter. If the actual measured voltages are different from the reference condition referred to with regard to FIG. 5, Np and Nn are recalculated to produce final values termed Np_final and Nn_final.

At 400, the device (e.g., the transmitter 120) is turned on. Initializing the transmitter causes the transmitter to configure itself as illustrated in FIG. 6. The encoder 200 (FIG. 3) of the transmitter 120 may perform some or all of these operations. At 402, the method includes measuring the pulser supply voltage, termed sup_p. As noted above, the pulser supply may vary from application to application and thus the disclosed method measures the actual supply voltage used for the transmitter.

At 404, the method also measures the handle supply voltage (termed sup_h). This measurement may be performed using the same or similar circuit as shown in FIG. 3 but with the supply to be measured being the handle supply voltage.

At 406, the source-to-handle voltage for MP1 is calculated. This voltage (termed Vsh_p_actual) may be calculated as the difference of the measured pulser supply voltage and the measured handle supply voltage. That is, Vsh_p_actual=sup_p−sup_h. Similarly, the source-to-handle voltage for MN1 is calculated at 408. This voltage (termed Vsh_n_actual) may be calculated as the difference of the negative of the measured pulser supply voltage and the measured handle supply voltage. That is, Vsh_p_actual=−sup_p−sup_h.

At 410, the method determines the final number of transistor units to use for MP1 (termed Np_final) as the trim value Np (that is, Np_final=Np). At 412, the method determines the final number of transistor units to use for MN1 (termed Nn_final). This calculation comprises:

$$Nn\_final = Nn[1+\alpha p(Vsh\_p\_actual - Vsh\_p\_ref) - \alpha n(Vsh\_n\_actual - Vsh\_n\_ref)]$$

The values of Np_final and Nn_final are determined by the encoder to generate the n-bit digital output value to be provided the decoder 250. The decoder 250 then asserts the control signals to the individual transistor unit signal paths to activate and deactivate the individual transistor units to implement the Np_final number of MP1 transistor units and the Nn_final number of MN1 transistor units.

Certain terms have been used throughout this description and claims to refer to particular system components. As one skilled in the art will appreciate, different parties may refer to a component by different names. This document does not intend to distinguish between components that differ in name but not function. In this disclosure and claims, the terms "including" and "comprising" are used in an open-ended fashion, and thus should be interpreted to mean "including, but not limited to . . . ." Also, the term "couple" or "couples" is intended to mean either an indirect or direct wired or wireless connection. Thus, if a first device couples to a second device, that connection may be through a direct connection or through an indirect connection via other devices and connections. The recitation "based on" is intended to mean "based at least in part on." Therefore, if X is based on Y, X may be a function of Y and any number of other factors.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A semiconductor device, comprising:
   a high side transistor comprising a plurality of selectable first transistor units;
   a low side transistor coupled in series with the high side transistor, wherein the low side transistor comprise a plurality of selectable second transistor units;
   trim storage configured to store trim values; and
   an encoder configured to:
      determine a magnitude of a supply voltage;
      determine a magnitude of a handle voltage;
      determine a source-to-handle voltage of the high side transistor;
      determine a source-to-handle voltage of the low side transistor;
      determine a target number of the selectable first transistor units to select for the high side transistor;
      determine a target number of the selectable second transistor units to select for the low side transistor based on a trim value, the source-to-handle voltage of the high side transistor and the source-to-handle voltage of the low side transistor, assert control signals to gate drivers associated with the selectable first and second transistor units to select the target number of selectable first transistor units and the target number of selectable second transistor units.

2. The semiconductor device of claim 1, wherein the trim value used by the encoder to determine the target number of the selectable second transistor units to select for the low side transistor comprises a value that is based on a measurement of saturation current of at least one of the high side transistor and low side transistor.

3. The semiconductor device of claim 1, wherein the trim value used by the encoder to determine the target number of the selectable second transistor units to select for the low side transistor comprises a value that is based on a calculated number of selectable first transistor units and a calculated number of second transistor units that results in saturation current of the high side transistor approximately matching the saturation current of the low side transistor.

4. The semiconductor device of claim 1, wherein the trim storage comprises:
   a first trim value equal to a maximum number of the selectable first transistor units or selectable second transistor units; and
   a second trim value computed based on a ratio of a measurement of saturation current of one of the high or low side transistors to a measurement of saturation current of the other of the high or low side transistors.

5. The semiconductor device of claim 4, wherein the trim storage comprises:
   a third trim value computed based on a measurement of the saturation current and a source-to-handle voltage of the high side transistor measured using a reference supply voltage and based on a measurement of the saturation current and the source-to-handle voltage the high side transistor using a test supply voltage; and
   a fourth trim value computed based on a measurement of the saturation current and a source-to-handle voltage of the low side transistor measured using the reference supply voltage and based on a measurement of the saturation current and the source-to-handle voltage the low side transistor using the test supply voltage.

6. The semiconductor device of claim 1, further comprising an ultrasound transducer coupled to the high and low side transistors.

7. The semiconductor device of claim 1, further comprising a plurality of comparators to compare a voltage indicative of the supply voltage to a plurality of first threshold voltages and a plurality of comparators to compare a voltage indicative of the handle voltage to a second plurality of threshold voltages.

8. A method, comprising:
   setting a first source-to-handle voltage for a first transistor, wherein the first transistor comprises a plurality of selectable first transistor units;
   setting a second source-to-handle voltage for a second transistor coupled to the first transistor, wherein the second transistor comprises a plurality of selectable second transistor units;

measuring a first saturation current of the first transistor;
measuring a second saturation current of the second transistor;
determining a number of the plurality of selectable first transistor units;
determining a number of the plurality of selectable second transistor units;
setting a third source-to-handle voltage for the first transistor;
setting a fourth source-to-handle voltage for a second transistor;
measuring a third saturation current of the first transistor;
measuring a fourth saturation current of the second transistor;
determining trim values based on the measured first, second, third, and fourth saturation currents; and
storing the trim values in a memory device.

9. The method of claim 8, wherein a first of the trim values is determined based on a difference in the first and third saturation currents and further based on a difference in the first and third source-to-handle voltages.

10. The method of claim 9, wherein a second of the trim values is determined based on a difference in the second and fourth saturation currents and further based on a difference in the second and fourth source-to-handle voltages.

11. The method of claim 10, wherein:
the first of the trim values is based on a ratio of the difference in the first and third saturation currents to the difference in the first and third source-to-handle voltages; and
the second of the trim values is based on a ratio of the difference in the second and fourth saturation currents to the difference in the second and fourth source-to-handle voltages.

12. The method of claim 8, wherein the trim values include values indicative of the first and second source-to-handle voltages.

13. The method of claim 8, wherein the trim values include values indicative of the first and second source-to-handle voltages and the determined numbers of the plurality of selectable first and second transistor units.

14. The method of claim 8, wherein:
responsive to the first saturation current being larger than the second saturation current, determining the number of the plurality of selectable first transistor units includes determining a ratio of the second saturation current to the first saturation current; and
determining the number of the plurality of selectable second transistor units includes setting the number of the plurality of selectable second transistor units to a maximum number of the plurality of selectable second transistor units comprising the second transistor.

15. The method of claim 8, wherein:
responsive to the first saturation current being smaller than the second saturation current, determining the number of the plurality of selectable second transistor units includes determining a ratio of the first saturation current to the second saturation current; and
determining the number of the plurality of selectable first transistor units includes setting the number of the plurality of selectable first transistor units to a maximum number of the plurality of selectable first transistor units comprising the first transistor.

16. A semiconductor device, comprising:
trim storage configured to store trim values; and
an encoder configured to:
determine a magnitude of a supply voltage;
determine a magnitude of a handle voltage;
determine a source-to-handle voltage of a first transistor;
determine a source-to-handle voltage of a second transistor;
determine a target number of selectable first transistor units comprising the first transistor to select for the first transistor;
determine a target number of selectable second transistor units comprising the second transistor to select for the second transistor;
based on a trim value from the trim storage, the source-to-handle voltage of the first transistor and the source-to-handle voltage of the second transistor, assert control signals to select the target number of selectable first transistor units and the target number of selectable second transistor units.

17. The semiconductor device of claim 16, wherein the trim value used by the encoder to determine the target number of the selectable second transistor units to select for the second transistor comprises a value that is based on a measurement of saturation current or on-resistance of at least one of the high side transistor and low side transistor.

18. The semiconductor device of claim 16, wherein the trim value used by the encoder to determine the target number of the selectable second transistor units to select for the second transistor comprises a value that is based on a calculated number of selectable first transistor units and a calculated number of second transistor units that results in saturation current of the first transistor approximately matching saturation current of the second transistor.

19. The semiconductor device of claim 16, wherein the trim storage comprises:
a first trim value equal to a maximum number of the selectable first transistor units or selectable second transistor units; and
a second trim value computed based on a ratio of a measurement of saturation current of one of the first or second transistors to a measurement of saturation current of the other of the first or second transistors.

20. The semiconductor device of claim 19, wherein the trim storage comprises:
a third trim value computed based on a measurement of the saturation current and a source-to-handle voltage of the first transistor measured using a reference supply voltage and based on a measurement of the saturation current and the source-to-handle voltage the first transistor using a test supply voltage; and
a fourth trim value computed based on a measurement of the saturation current and a source-to-handle voltage of the second transistor measured using the reference supply voltage and based on a measurement of the saturation current and the source-to-handle voltage the second transistor using the test supply voltage.

* * * * *